US006559121B2

(12) United States Patent
Pruett et al.

(10) Patent No.: US 6,559,121 B2
(45) Date of Patent: May 6, 2003

(54) VACCINES FOR THE PROTECTION OF CATTLE FROM PSOROPTIC SCABIES

(75) Inventors: John H. Pruett, Kerrville, TX (US); Kevin B. Temeyer, Boerne, TX (US); Sidney E. Kunz, Kerrville, TX (US); William F. Fisher, Kerrville, TX (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 09/860,793

(22) Filed: May 18, 2001

(65) Prior Publication Data

US 2002/0136734 A1 Sep. 26, 2002

Related U.S. Application Data

(62) Division of application No. 09/366,603, filed on Aug. 3, 1999, now abandoned.

(60) Provisional application No. 60/089,666, filed on Jun. 17, 1998.

(51) Int. Cl.$^7$ ........................ A01K 37/18; A61K 38/00; A61K 39/00; A61K 39/12; A61K 39/35; A61K 39/36; C07K 1/00; C07K 14/00; C07K 17/00

(52) U.S. Cl. ..................... 514/2; 424/184.1; 424/185.1; 424/275.1; 530/350

(58) Field of Search ........................... 424/171.1, 184.1, 424/185.1, 191.1, 279.1, 275.1, 276.1; 435/69.1, 70.21, 91.1; 514/1; 530/300, 355, 324–27, 350; 536/23.5, 23.1, 23.4

(56) References Cited

FOREIGN PATENT DOCUMENTS

GB WO 97/42418 * 11/1997

OTHER PUBLICATIONS

Jayawardena et al, "Antigens of the sheep scab mite Psoroptes ovis," Folia Parasitologica, vol. 45, pp. 239–244 (1998).*

Pruett et al., "Evaluation of natural Psoroptes ovis (Acarina: Psoropidae) soluble proteins as candidate vaccine immunogens", JOurnal of Medical Entomology, vol. 35, pp. 861–871 (1998).*

Matthes et al, "Cross–reacting Antibodies to Sarcoptes suis, Chorioptes bovis, and Notoedres cati and anti–P. ovis IgE in Sera from Sheep infested Naturally with Psorptes ovis," International Journal of Parasitology, vol. 26, pp. 437–444 (1996).*

* cited by examiner

*Primary Examiner*—James Housel
*Assistant Examiner*—Zachariah Lucas
(74) *Attorney, Agent, or Firm*—John D. Fado; Randall E. Deck

(57) ABSTRACT

A novel antigenic protein which is effective for stimulating antibody production in animals against the sheep scab mite, *Psoroptes ovis* is disclosed. In cattle, administration of the protein provides protection from infestation by *P. ovis* by eliciting an immediate-type hypersensitivity response and/or immunizing the animal against *P. ovis.* The protein is also effective for producing and/or binding antibodies to *P. ovis,* and may be used as an immunodiagnostic reagent.

3 Claims, 6 Drawing Sheets

*Psoroptes ovis* cDNA gene sequence & translation for 16 kD allergen

```
                                      1        10        20        30        40        50
cDNA                                  5'-CCTCGCGGCCTCGTCGACCCCAATTAAAACTAAAAAATAATTTTAAAAAAATCAAA-
Translation

              60          70          80          90          100         110
cDNA          ATG ATG AAA ACT TTG GTA GTT CTC GCC ATC ACT TTG GCT GTT GTA TCA GCT GGS AAR GTC
Translation   Met Met Lys Thr Leu Val Val Leu Ala Ile Thr Leu Ala Val Val Ser Ala Gly Lys Val

              120         130         140         150         160         170
cDNA          AAR TTY CAA GAC TGT GGA AAA GGR GAA GTT GAA TCT CTT GAA GTT GAA GGC TGT TCA GGT
Translation   Lys Phe Gln Asp Cys Gly Lys Gly Glu Val Glu Ser Leu Glu Val Glu Gly Cys Ser Gly

              180         190         200         210         220         230
cDNA          GAT TAC TGC GTC ATT CAC AAA GGT AAA AAA CTT GAT TTA GCC ATC AGT GTA ACA TCG AAC
Translation   Asp Tyr Cys Val Ile His Lys Gly Lys Lys Leu Asp Leu Ala Ile Ser Val Thr Ser Asn

              240         250         260         270         280         290
cDNA          CAA GAT TCA GCC AAT TTG AAA CTC GAT ATT GTT GCC GAT ATC AAC GGT GTA CAA ATT GAA
Translation   Gln Asp Ser Ala Asn Leu Lys Leu Asp Ile Val Ala Asp Ile Asn Gly Val Gln Ile Glu

              300         310         320         330         340         350
cDNA          GTT CCT GGC GTT GAT CAT GAT GGT TGC CAT TAC GTC AAA TGT CCA ATC AAG AAA GGC CAA
Translation   Val Pro Gly Val Asp His Asp Gly Cys His Tyr Val Lys Cys Pro Ile Lys Lys Gly Gln

              360         370         380         390         400         410
cDNA          CAC TTT GAC GTC AAA TAC ACA TAC AGC ATT CCA GCA ATC TTG CCA ACT ACC AAA GCT AAA
Translation   His Phe Asp Val Lys Tyr Thr Tyr Ser Ile Pro Ala Ile Leu Pro Thr Thr Lys Ala Lys

              420         430         440         450         460         470
cDNA          ATC ATT GCT AAA ATT ATT GGT GAT AAA GGT CTT GGT GGT TGT ATC GTA ATC AAT GGT GAA
Translation   Ile Ile Ala Lys Ile Ile Gly Asp Lys Gly Leu Gly Gly Cys Ile Val Ile Asn Gly Glu

              480         490       500       510        520       530       540      550
cDNA          ATT CAA GAC TAA-ATCAATAAAAACCTAAAAATATTTTGATGAAATTAGATTTGTTATTTTTATTTCTCATTTTAT
Translation   Ile Gln Asp STOP

                 560       570       580
cDNA          TCAAAATTAAAAAGTATTCAGTCGACGAGGCCGCGAG-3'
```

```
Sequence Range: 1 to 90
                 10                  20                  30                    40                  50
                  *                   *                   *                     *                   *
GGN AAR GTN AAR TTY CAR GAY TGY GGN AAR GGN GAR GTN GAR WSN YTN GAR GTN
CCN TTY CAN TTY AAR GTY CTR ACR CCN TTY CCN CTY CAN CTY WSN RAN CTY CAN
Gly Lys Val Lys Phe Gln Asp Cys Gly Lys Gly Glu Val Glu Ser Leu Glu Val>
___a___a___a___REVERSE-TRANSLATION OF P.OVIS16K/N1-30AA____a___a___a___>

        60                  70                  80                  90
         *                   *                   *                   *
GAR GGN TGY WSN GGN GAY TAY TGY GTN ATH CAY AAR
CTY CCN ACR WSN CCN CTR ATR ACR CAN TAD GTR TTY
Glu Gly Cys Ser Gly Asp Tyr Cys Val Ile His Lys>
___REVERSE-TRANSLATION OF P.OVIS16K/N1-30AA____>
```

FIG. 3

5'-CCTCGCGGCCTCGTCGACCCCAATTAAAACTAAAAAATAATTTTAAAA
AAATCAAA*ATGATGAAAACTTTGGTAGTTCTCGCCATCACTTTGGCTGTTGTATCA*
*GCT*GGSAARGTCAARTTYCAAGACTGTGGAAAAGGRGAAGTTGAATCTCT
TGAAGTTGAAGGCTGTTCAGGTGATTACTGCGTCATTCACAAAGGTAAAA
AACTTGATTTAGCCATCAGTGTAACATCGAACCAAGATTCAGCCAATTTG
AAACTCGATATTGTTGCCGATATCAACGGTGTACAAATTGAAGTTCCTGG
CGTTGATCATGATGGTTGCCATTACGTCAAATGTCCAATCAAGAAAGGCC
AACACTTTGACGTCAAATACACATACAGCATTCCAGCAATCTTGCCAACT
ACCAAAGCTAAAATCATTGCTAAAATTATTGGTGATAAAGGTCTTGGTGG
TTGTATCGTAATCAATGGTGAAATTCAAGACTAAATCAATAAAAACCTAAA
AATATTTTGATGAAATTAGATTTGTTATTTTTATTTCTCATTTTATTCAAAATT
AAAAAGTATTCAGTCGACGAGGCCGCGAG-3'

FIG. 4

MMKTLVVLAITLAVVSAGKVKFQDCGKGEVESLEVEGCSGDYCVIHKGKKLDL
AISVTSNQDSANLKLDIVADINGVQIEVPGVDHDGCHYVKCPIKKGQHFDVKYTY
SIPAILPTTKAKIIAKIIGDKGLGGCIVINGEIQD

FIG. 5

```
16 kDa    1 KVKFQDCGKGEVESLEVEGCSGDYCV 26
            K+  F+DCG GEV  L++ GCSGD CV
Lep d I  18 KMTFKDCGHGEV TELDI SGCSGDTCV 43

16 kDa    1 KVKFQDCGKGEVESLEVEGCSG 22
            +V   +DC    E++ + V+GC G
Der f II  2 QVDVKD CANNE IKKVMVDGCHG 23
```

VACCINES FOR THE PROTECTION OF CATTLE FROM PSOROPTIC SCABIES

BACKGROUND OF THE INVENTION

1. Field of the Invention

The invention relates to a novel protein from the sheep scab mite, *Psoroptes ovis,* which may be used for eliciting host-protective grooming behavior and/or immune response in cattle.

2. Description of the Prior Art

*Psoroptes ovis* (Hering) (Acarina: Psoroptidae), the globally distributed sheep scab mite, is an economically important parasite of domestic cattle and sheep, and a serious threat to wild populations of bighorn sheep (Boyce & Brown, 1991, J. Parasitol. 77:675–679). Mite infestation of susceptible cattle can result in the development of scabies lesions. The lesion is consistent with allergic dermatitis (Stromberg & Fisher, 1986, Am. J. Vet. Res., 47:1551–1560) characterized histologically by superficial perivascular dermatitis, marked edema in the superficial dermis, numerous eosinophils, and mast cells (Stromberg & Guillot, 1989, Am. J. Vet. Res., 50: 594–601). The dermatitis can become extensive and lead to the death of cattle in poor condition, and under extremes of environmental stress. It has been suggested that death may occur as a result of the high demand, and consumption of neutrophils at the lesion site, leaving other tissues such as the lungs susceptible to secondary bacterial infection (Stromberg & Guillot, 1987, Vet. Pathol., 24: 365–370).

Stanchioned cattle repeatedly infested with *P. ovis* appear to develop some level of resistance, defined by a slower rate of lesion and mite population growth (Stromberg & Fisher, 1986, ibid). Guillot & Stromberg (1987, Vet. Parasitol., 10:73–78) suggested that the slow progression of lesion and mite population expansion on stanchioned resistant cattle could be attributed to a lowered ovipositional rate of the female mites, by some unexplained mechanism. Losson et al. (1988, Res. Vet. Sci., 44:197–201) reexposed unstanchioned cattle to *P. ovis* and the cattle exhibited signs of immediate hypersensitivity including pruritus, scratching, and exudation. Scabies lesions developed on these cattle but healed rapidly and none of the cows developed clinical scabies.

Unfortunately, knowledge of the immunogenicity and allergenicity of purified *P. ovis* proteins in cattle is limited. In an effort to qualitatively describe mite proteins to which cattle respond, Boyce and Brown (1991, ibid) electrophoretically resolved Psoroptes spp. crude soluble proteins from cattle collected mites. These separated proteins were immunoblotted with serum from a moderately P. spp. infested cow. They found that<20 antigens were recognized by antibody in this serum, with bands at 10 and 116 kDa being most prominent. Mathes et al. (1996, Int. J. Parasitol., 26:437–444), working with immune serum from *P. ovis* infested sheep and crude *P. ovis* proteins, detected approximately 24 antigenic proteins with dominant bands at 15, 44, 130, and 170 kDa.

Behavioral self-grooming has been shown in other cattle/ectoparasite systems to account for a significant reduction in the ectoparasite numbers (Koudstaal et al., 1978, Parasitol., 76:379–386). Fisher and Wright [1981, Southwestern Entomolog., 6(1):57–61], Guillot (1981, J. Econ. Entomol., 74:653–657) and Losson et al. (1988, ibid) suggested that the stimulation of self-grooming in cattle was significant in natural acquired resistance to *P. ovis* infestation.

SUMMARY OF THE INVENTION

We have discovered a novel antigenic protein which is effective for stimulating antibody production, resulting at least in part in an immediate-type hypersensitivity reaction, in cattle against the sheep scab mite, *Psoroptes ovis.* In cattle, administration of the protein provides protection from infestation by *P. ovis* by eliciting a grooming response and/or immunizing the animal against *P. ovis.* The protein is also effective for producing and/or binding antibodies to *P. ovis,* and may be used as an immunodiagnostic reagent. The invention also includes isolated DNA sequences encoding the protein, expression vectors containing these sequences, microorganisms or other host cells transformed with these vectors, and recombinant methods for producing the protein.

In accordance with this discovery, it is an object of this invention to provide a protein which is effective for protecting cattle against infestation with *P. ovis.*

It is also an object of this invention to provide a protein which is effective for either or both of eliciting an immediate-type hypersensitivity reaction and thus cause a grooming response in cattle against *P. ovis,* or immunizing the cattle against this pest.

Another object of this invention is to provide a protein effective for producing antibodies which selectively bind to *P. ovis* for use in assays for this pest.

Yet another object of this invention is to provide a protein which will bind to antibodies made in a host to *P. ovis* and may be used as an immunodiagnostic reagent.

Still another object of this invention is to provide the genes which encode the protein, which may be used to provide recombinant DNA molecules containing the genes for insertion into host cells and expression of the protein therefrom.

Other objects and advantages of this invention will become readily apparent from the ensuing description.

BRIEF DESCRIPTION OF THE DRAWINGS

FIG. 1 shows one nucleotide sequence of the cDNA gene coding for the antigenic 16 kDa *P. ovis* protein of this invention as well as the corresponding predicted amino acid sequence of the protein.

FIG. 2 shows the reverse translation of N-terminal amino acids 1–30 of *P. ovis* 16 kDa protein.

FIG. 3 shows the nucleotide sequence of the cDNA gene coding for the antigenic 16 kDa *P. ovis* protein of this invention as determined in Example 1. The underlined sequence corresponds to the reverse translation of the 30 N-terminal amino acids obtained by microsequencing the isolated 16 kDa protein of *P. ovis.* Sequence in bold type is translated to the predicted mature *P. ovis* 16 kDa protein with an additional 16–17 amino acid peptide leader sequence commencing with two tandem translational start codons specified by the italic type (beginning with ATGATG . . . ).

FIG. 4 shows the amino acid sequence for the precursor to the 16 kDa protein of *P. ovis* deduced from cDNA translation in Example 1.

FIG. 5 shows the alignment of amino acids 2–26 of the mature N-terminal *P. ovis* 16 kDa protein with allergens of the storage mite *Lepidoglyphus destructor* and the house-dust mite *Dermatophagoides farinae.*

DEFINITIONS

Figure 6:
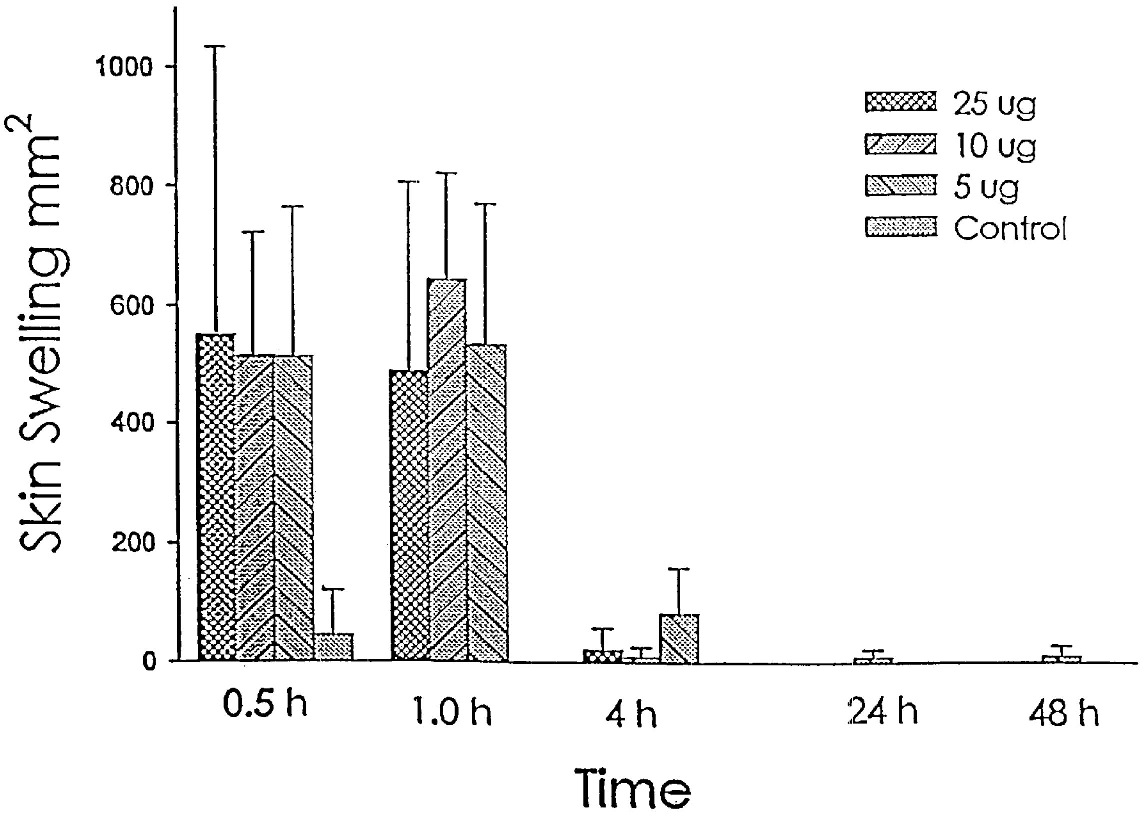
FIG. 6 shows the intradermal skin test results of calves vaccinated with different dosages of the *P. ovis* 16 kDa protein.

The following terms are employed herein:

Cloning. The selection and propagation of (a) genetic material from a single individual, (b) a vector containing one gene or gene fragment, or (c) a single organism containing one such gene or gene fragment.

Cloning Vector. A plasmid, virus, retrovirus, bacteriophage or nucleic acid sequence which is able to replicate in a host cell, characterized by one or a small number of restriction endonuclease recognition sites at which the sequence may be cut in a predetermined fashion, and which contains a marker suitable for use in the identification of transformed cells, e.g., tetracycline resistance or ampicillin resistance. A cloning vector may or may not possess the features necessary for it to operate as an expression vector.

Codon. A DNA sequence of three nucleotides (a triplet) which codes (through mRNA) for an amino acid, a translational start signal, or a translational termination signal. For example, the nucleotide triplets TTA, TTG, CTT, CTC, CTA, and CTG encode for the amino acid leucine, while TAG, TAA, and TGA are translational stop signals, and ATG is a translational start signal.

DNA Coding Sequence. A DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, procaryotic sequences and CDNA from eucaryotic mRNA. A polyadenylation signal and transcription termination sequence will usually be located 3' to the coding sequence.

DNA Sequence. A linear series of nucleotides connected one to the other by phosphodiester bonds between the 3' and 5' carbons of adjacent pentoses.

Expression. The process undergone by a structural gene to produce a polypeptide. Expression requires both transcription of DNA and translation of RNA.

Expression Vector. A replicon such as a plasmid, virus, retrovirus, bacteriophage, or nucleic acid sequence which is able to replicate in a host cell, characterized by a restriction endonuclease recognition site at which the sequence may be cut in a predetermined fashion for the insertion of a heterologous DNA sequence. An expression vector has a promoter positioned upstream of the site at which the sequence is cut for the insertion of the heterologous DNA sequence, the recognition site being selected so that the promoter will be operatively associated with the heterologous DNA sequence. A heterologous DNA sequence is "operatively associated" with the promoter in a cell when RNA polymerase which binds the promoter sequence transcribes the coding sequence into mRNA which is then in turn translated into the protein encoded by the coding sequence.

Fusion Protein. A protein produced when two heterologous genes or fragments thereof coding for two different proteins not found fused together in nature are fused together in an expression vector. For the fusion protein to correspond to the separate proteins, the separate DNA sequences must be fused together in correct translational reading frame.

Gene. A segment of DNA which encodes a specific protein or polypeptide, or RNA.

Genome. The entire DNA of an organism. It includes, among other things, the structural genes encoding for the polypeptides of the substance, as well as operator, promoter and ribosome binding and interaction sequences.

Heterologous DNA. A DNA sequence inserted within or connected to another DNA sequence which codes for polypeptides not coded for in nature by the DNA sequence to which it is joined. Allelic variations or naturally occurring mutational events do not give rise to a heterologous DNA sequence as defined herein.

Hybridization. The pairing together or annealing of single stranded regions of nucleic acids to form double-stranded molecules.

Nucleotide. A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. The base characterizes the nucleotide. The four DNA bases are adenine ("A"), guanine ("G"), cytosine ("C"), and thymine ("T"). The four RNA bases are A, G, C, and uracil ("U").

Phage or Bacteriophage. Bacterial virus many of which include DNA sequences encapsidated in a protein envelope or coat ("capsid"). In a unicellular organism a phage may be introduced by a process called transfection.

Plasmid. A non-chromosomal double-stranded DNA sequence comprising an intact "replicon" such that the plasmid is replicated in a host cell. When the plasmid is placed within a unicellular organism, the characteristics of that organism may be changed or transformed as a result of the DNA of the plasmid. A cell transformed by a plasmid is called a "transformant."

Polypeptide. A linear series of amino acids connected one to the other by peptide bends between the alpha-amino and carboxy groups of adjacent amino acids.

Promoter. A DNA sequence within a larger DNA sequence defining a site to which RNA polymerase may bind and initiate transcription.

Reading Frame. The grouping of codons during translation of mRNA into amino acid sequences. During translation the proper reading frame must be maintained. For example, the DNA sequence may be translated via mRNA into three reading frames, each of which affords a different amino acid sequence.

Recombinant DNA Molecule. A hybrid DNA sequence comprising at least two DNA sequences, the first sequence not normally being found together in nature with the second.

Ribosomal Binding Site. A nucleotide sequence of mRNA, coded for by a DNA sequence, to which ribosomes bind so that translation may be initiated. A ribosomal binding site is required for efficient translation to occur. The DNA sequence coding for a ribosomal binding site is positioned on a larger DNA sequence downstream of a promoter and upstream from a translational start sequence.

Replicon. Any genetic element (e.g., plasmid, chromosome, virus) that functions as an autonomous unit of DNA replication in vivo, i.e., capable of replication under its own control.

Start Codon. Also called the initiation codon, is the first mRNA triplet to be translated during protein or peptide synthesis and immediately precedes the structural gene being translated. The start codon is usually AUG, but may sometimes also be GUG.

Structural Gene. A DNA sequence which encodes through its template or messenger RNA (mRNA) a sequence of amino acids characteristic of a specific polypeptide.

Transform. To change in a heritable manner the characteristics of a host cell in response to DNA foreign to that cell. An exogenous DNA has been introduced inside the cell wall or protoplast. Exogenous DNA may or may not be integrated (covalently linked) to chromosomal DNA making up the genome of the cell. In procaryotes and yeast, for example, the exogenous DNA may be maintained on an episomal element such as a plasmid. With respect to eucaryotic cells, a stably transformed cell is one in which the exogenous DNA has been integrated into a chromosome so that it is inherited by daughter cells through chromosome replication. This stability is demonstrated by the ability of the eucaryotic cell to establish cell lines or clones comprised of a population of daughter cells containing the exogenous DNA.

Transcription. The process of producing mRNA from a structural gene.

Translation. The process of producing a polypeptide from mRNA.

DETAILED DESCRIPTION OF THE INVENTION

In the following description, the nomenclature used to define the proteins is that specified by Schroder and Lubke ["The Peptides," Academic Press (1965)] wherein, in accordance with conventional representation, the N-terminal appears to the left and the C-terminal to the right. Where the amino acid residue has isomeric forms, it is the L-form of the amino acid that is represented herein unless otherwise expressly indicated.

The present invention provides an antigenic protein effective for eliciting antibody production and a local immediate-type hypersensitivity reaction in an animal against the sheep scab mite, *Psoroptes ovis.* Elicitation of immediate-type hypersensitivity to the protein will in turn result in a grooming or scratching behavior by the treated animal localized to any site(s) of exposure to this mite, thereby partially protecting the animal from infestation. While it is envisioned that the protein is capable of eliciting these responses in a variety of animals against *P. ovis,* in the preferred embodiment the protein is used for eliciting antibody production in cattle, including beef or dairy cattle of the genus Bos.

The mature, native form of the protein of the invention has a molecular weight of about 16 kDa as determined by sodium dodecyl sulfate polyacrylamide gel electrophoresis (SDS-PAGE). The N-terminal amino acid sequence of the mature form of the natural protein has been determined as $X_1$KVKFQDCGKGEVESLEVEGCSGDY wherein $X_1$ is either G, S or V. It is understood that some forms of the protein may have additional N-terminal amino acids which may occur, for example, as a result of incomplete processing or hydrolysis of the signal sequence. The protein may also be covalently bonded to a non-related fusion protein as described in greater detail hereinbelow. The invention also encompasses substantial equivalents of this protein which retain the ability to elicit antibody production in an animal against *P. ovis.* The practitioner of ordinary skill in the art will recognize that slight deviations of the amino acid sequences may be made without affecting the immunogenicity of the protein. Substantial equivalents of the above protein include conservative substitutions of amino acids with other amino acids, including either naturally occurring or non-conventional amino acids, which maintain substantially the same charge and hydrophobicity as the original amino acid. Conservative substitutions include for example, replacement of glycine for alanine, valine for isoleucine, leucine for isoleucine, aspartic acid for glutamic acid, lysine for arginine, asparagine for glutamine, phenylalanine for tryptophan, and tryptophan for tyrosine. Examples of conservative substitutions with non-conventional amino acids are described in Rosenberg et al. (U.S. Pat. No. 5,679,782) the contents of which are incorporated by reference herein.

The protein may be isolated from any *P. ovis* mite to pure or substantially pure form which is free of endogenous *P. ovis* material using the techniques described in Example 1 hereinbelow. In brief, *P. ovis* mites are ground in a suitable buffered aqueous solvent to solubilize the proteins therein. A conventional protease inhibitor such as phenylmethylsulfonylfluoride (PMSF), may be added to inhibit protein hydrolysis. Solids and cellular material may be separated, for example, by centrifugation and/or filtration, with the supernatant containing a crude mixture of soluble *P. ovis* proteins being retained. The soluble protein may then be fractionated by molecular size using conventional molecular sieve chromatography, and the relatively low molecular weight band(s) encompassing 16 kDa retained. Purification of the 16 kDa within this band may be accomplished by continuous elution sodium dodecyl sulfate polyacrylamide gel electrophoresis (SDS-PAGE).

In use, it is envisioned that the isolated protein will typically be formulated in conjunction with a suitable inert carrier or vehicle as known in the art. The skilled practitioner will recognize that such carriers should of course be compatible with the protein. The concentration and amount of the protein in the final composition may vary depending upon the desired use and type of response needed, and the host animal. In any event, the protein should be employed in an amount effective to induce the preferred response as determined by routine testing.

When the protein is used to elicit antibody production against *P. ovis,* the proteins may be formulated with a physiologically acceptable diluent or carrier such as phosphate buffered saline. The proteins may be administered to a target animal by any convenient route, including intramuscularly, intraperitonealy or preferably subcutaneously, in a single dose or in a plurality of doses. The protein may also be administered in combination with optional stabilizers and immunopotentiating agents or adjuvants. Typical stabilizers include, for example, sucrose, an alkali metal hydrogen phosphate salt, glutamate, serum albumin, gelatin, or casein. A variety of adjuvants are suitable for use herein, although a mixture of alhydrogel and amphigen is preferred. Other conventional adjuvants which may be suitable for use herein include those described by Davis et al. (ed.) (Microbiology, second edition, Harper & Row, Hagerstown, Md., 1973, pp. 480–482), the contents of which are incorporated by reference herein. The proteins may be stored under refrigeration or in frozen or lyophilized form.

In a preferred embodiment, the objective of antibody production is the protection of cattle against *P. ovis* by eliciting antibody production and/or an immediate-type hypersensitivity in the animal. Generally, the proteins are administered to the target animal in an amount effective to elicit either or both of these responses in a subject animal as compared to an untreated control. The effective amount will vary with the particular target animal, its age and size, and may be readily determined by the practitioner skilled in the art. Without being limited thereto, typical doses for treatment of cattle may be greater than 5 $\mu$g/animal/dose, preferably between 5 to 25 $\mu$g/animal/dose administered by subcutaneous or intramuscular injection.

In a variation of this preferred embodiment, the antibodies so-produced in the host animal may be recovered for use in a diagnostic assay for the identification of *P. ovis.* While mites are typically identified on the basis of clinical observations and microscopic examination, identification by immunoassay with the antibodies may aid in the identification of *P. ovis,* particularly when a trained acarologist is unavailable. A variety of conventional immunoassay techniques are suitable for use herein, including RIA, or ELISA, or double antibody sandwich immunoassays.

In an alternative embodiment, the protein may be used as an immunodiagnostic reagent for binding and detecting antibodies in the serum of an animal. Detection of antibodies against *P. ovis* in the sera of animals may be used for monitoring and detecting animals which are carriers of the mites but which do not show outward signs of infestation, as well as identifying animals previously exposed or infested with *P. ovis.* Again, a variety of conventional immunoassays are suitable for use herein, although ELISA are preferred. For example, in such an ELISA test, the purified protein of this invention may be used as an antigen bound to the wells of a microtiter plate. Following contact of the test animal sera with the adsorbed antigen, bound anti-*P. ovis* antibodies may then be detected.

The invention also encompasses isolated DNA sequences, free of homologous DNA, which encode the above-described 16 kDa *P. ovis* protein. The DNA sequence coding for the protein was derived from cDNA synthesized from *P. ovis* mRNA as described in Example 1 hereinbelow and is shown in FIGS. 1 and 3. The complete predicted amino acid sequence of the encoded *P. ovis* protein is also shown in FIGS. 1 and 4. As shown in FIG. 1, translation starts with a 17 amino acid leader peptide (in italics) which is not present in the mature protein. The first 30 N-terminal amino acids of the mature protein are underlined and agree perfectly with the microsequence obtained from the mature protein described in Example 1 hereinbelow. The total cDNA sequence is 588 nucleotides in length which codes for 143 amino acids, of which 126 are present in the mature protein after cleavage of the leader (signal) peptide. There are post-translational modification sites present.

Because of the degeneracy of the genetic code, there exists a finite set of nucleotide sequences which can code for a given amino acid sequence. It is understood that all such equivalent sequences are operable variants of the disclosed sequence, since all give rise to the same protein (i.e., the same amino acid sequence) during in vivo transcription and translation, and are hence encompassed by the instant invention. DNA sequences which are substantially homologous to the nucleotide sequences of FIGS. 1 and 3 are also encompassed by the invention. As defined herein, two DNA sequences are substantially homologous when at least 85% (preferably at least 90% and most preferably 95%) of the nucleotides match over the defined length of the sequence. Sequences that are substantially homologous can be identified in a Southern hybridization experiment under stringent conditions as is known in the art. See, for example, Maniatis et al., Molecular Cloning: A Laboratory Manual, Cold Springs Harbor Laboratory, 1982, or DNA Cloning: A Practical Approach, Vol. I and II (Ed. D. N. Glover), IRL Press, Oxford, 1985.

The DNA sequences of the invention can be used to prepare recombinant DNA molecules by cloning in any suitable vector. A variety of vector-host cell expression systems may be employed in practicing the present invention. Host cells may be either procaryotic or eucaryotic, and, when the host cells are bacterial cells, they may be either gram-negative or gram-positive bacteria. Strains of *Escherichia coli* are generally preferred for use in procaryotic systems. However, without being limited thereto, other useful hosts include species of Salmonella (including, for example, *S. typhimurium, S. enteriditis,* and *S. dublin*) species of Mycobacterium (such as *M. smegmatis* and *M. bovis,* species of Pseudomonas (including, for example, *P. aeruginosa* and *P. putida*), *Bacillus subtilis,* yeasts and other fungi (for example, *Saccharomyces cerevisiae*), plant cells such as plant cells in culture (including, for example, both angiosperms and gymnosperms) and animal cells such as animal cells in culture.

Vectors used in practicing the present invention are selected to be operable as cloning vectors or expression vectors in the selected host cell. Numerous vectors are known to practitioners skilled in the art, and selection of an appropriate vector and host cell is a matter of choice. The vectors may, for example, be bacteriophage, plasmids, viruses, or hybrids thereof. A number of procaryotic expression vectors are described in U.S. Pat. Nos. 4,652,525, 4,440,859, 4,436,815, and 4,342,832, and a number of eucaryotic expression vectors have also been described in U.S. Pat. Nos. 4,546,082, 4,510,245, 4,446,235, and 4,443,540. Further, the vectors may be non-fusion vectors (i.e., those producing the antigenic protein of the invention not fused to any heterologous polypeptide), or alternatively, fusion vectors (i.e., those producing the antigenic protein fused to a vector encoded polypeptide). The fusion proteins would of course vary with the particular vector chosen. Suitable non-fusion plasmid vectors for use with *E. coli* include but are not limited to pTrc99 for use with *E. coli* JM 105, or pANK-12, pANH-1 or pPL2 for use with *E. coli* MZ 1. Conversely, suitable fusion plasmid vectors include PGEX and pMC1871 for use with *E. coli* JM 105, pMAL with *E. coli* PR 722, pVB2 with *E. coli* LA5709, pTrcHis with *E. coli* INV F', pCO5 with *E. coli* N6405, and pRIT2T or pEZZ 18 with *E. coli* N4830-1. Other, non-*E. coli* expression systems which may also he employed include pAc360 or pBluescript for use with SP2 or High 5 insect cells, pYesHis with the yeast *S. cerevisiae* INVSc1 or INVSc2, pLS405 with *Salmonella dublin* SL598, and pYUB12 with *Mycobacterium smegmatis* or *M. bovis.* Still other suitable vector-host combinations that may be used in practicing the instant invention are described, for example, in U.S. Pat. Nos. 5,122,471 and 5,670,339 the contents of each of which are incorporated by reference herein.

Within each specific vector various sites may be selected for insertion of the isolated DNA sequence. These sites are usually designated by the restriction enzyme or endonuclease that cuts them. For example, in pBR322 the Pst I site is located in the gene for penicillinase between the nucleotide triplets that code for amino acids 181 and 182 of the penicillinase protein.

The particular site chosen for insertion of the selected DNA fragment into the vector to form a recombinant vector is determined by a variety of factors. These include size and structure of the polypeptide to be expressed, susceptibility of the desired polypeptide to enzymatic degradation by the host cell components and contamination by its proteins, expression characteristics such as the location of start and stop codons, and other factors recognized by those of skill in the art. None of these factors alone absolutely controls the choice of insertion site for a particular polypeptide. Rather, the site chosen reflects a balance of these factors, and not all sites may be equally effective for a given protein.

The DNA sequences of the invention may be inserted into the desired vector by known techniques. If, however, the vector is to serve as an expression vector, the vector should have a promoter, and the DNA sequence should be inserted in the vector downstream of the promoter and operationally associated therewith. While control sequences may be ligated to the coding sequence prior to insertion into the vector, preferably, the vector should be selected so as to have a promoter operable in the host cell into which the vector is to be inserted (that is, the promoter should be recognized by the RNA polymerase of the host cell). In addition, the vector should have a region which codes for a ribosome binding site positioned between the promoter and the site at which the DNA sequence is inserted so as to be operatively associated with the DNA sequence of the invention once inserted (in correct translational reading frame therewith). The vector should be selected to provide a region which codes for a ribosomal binding site recognized by the ribosomes of the host cell into which the vector is to be inserted.

The antigenic proteins of the invention are produced by growing host cells transformed by the expression vectors described above under conditions whereby the antigen is produced. The antigens are then isolated from the host cells. Depending on the host cell used, transformation is done using standard techniques. For example, the calcium treatment employing calcium chloride, as described by Cohen (1972, Proc Natl Acad Sci USA, 69:2110), or the RbC1 method described in Maniatis et al. (ibid, p. 254) may be used for procaryotes or other cells which contain substantial cell wall barriers. Infection with *Agrobacterium tumefaciens* such as described by Shaw (1983, Gene, 23:315) may be used for certain plant cells. For mammalian cells without such cell walls, the calcium phosphate precipitation method of Graham and Van der Eb (1978, Virology, 52:546) may be used. Transformations into yeast may be conducted, for example, according to the method of Van Solingen, et al., (1977, J. Bacter., 130:946), and Hsiao et al. (1979, Proc Natl Acad Sci USA, 76:3829).

In general, after construction of a suitable expression system, the system is transfected into the appropriate host and successful transformants may be selected by markers contained on the expression vectors. Successfully transformed colonies are then cultured in order to produce the protein. Optionally, a promoter which can be controlled by regulating conditions in the environment may be used such that the cells can be grown under conditions where the gene encoding the desired protein of the invention is not expressed, but production of the protein may be induced by appropriate manipulation of conditions, as described in U.S. Pat. No. 5,670,339. This protocol may be used to prevent premature accumulation of the protein which may be harmful to the growth of the cell.

The protein may be produced intracellularly, or in secreted form by construction of vectors wherein the peptide is preceded by a signal peptide workable in the appropriate host. The recombinant protein may then be recovered from the medium or from the cells using suitable techniques generally known in the art, and purified by, for example, ion exchange chromatography, ammonium sulfate precipitation, or gel permeation chromatography.

The following examples are intended only to further illustrate the invention and are not intended to limit the scope of the invention which is defined by the claims.

EXAMPLE 1

Preparation of Antigens

*P. ovis* soluble antigens (POI) were prepared by grinding age-mixed mites in a TenBroeck tissue grinder in 0.01 M Tris-HCl, pH 7.5 containing 1 mM PMSF. The solution of ground mites was centrifuged for 20 min at 4° C. at 2,530×g. The supernatant fluid was decanted and filtered at 5 $\mu$M (Gelman, ACRODISC, Ann Arbor, Mich.). The protein concentration of the supernatant fluid was determined by a modified Lowry (Bradshaw, 1966, Introduction to molecular biological techniques. Printice-Hall Inc., Englewood Cliffs, N.J., 107 pp). The soluble antigen preparation was stored at −20° C.

DEAE Anion Exchange Chromatography

The FI protein fraction was prepared by ion-exchange chromatography. POI proteins were applied to a column of DEAE SEPHACEL (Pharmacia Fine Chemicals, Uppsala, Sweden), and eluted with 0.01 M Tris-HCl, pH 7.5, over a linear gradient of NaCl ranging from 0.0 to 1.0 M.

SDS-PAGE and Western Blotting

POI and fractionated POI proteins were resolved on polyacrylamide gradient gels (3–22%). Briefly, proteins were resolved using a modified method of Laemmli (1970, Nature, 227:680–685) with reducing (2-mercaptoethanol, 2-ME) sodium dodecyl sulfate (SDS) discontinuous polyacrylamide gel electrophoresis (2ME-SDS-PAGE) with an LKB 2050 MIDGET electrophoresis unit (Pharmacia LKB Biotech., Pisdcataway, N.J.). Resolved proteins were transferred to nitrocellulose paper as described in Pruett & Thomas (1986, J. Insect Physiol., 32:9–16). Blots were challenged with specific animal serum and developed. Positive serum samples were obtained from infested stanchioned calves (wk 5 sera, #124, #125, #126), an unstanchioned infested calf (wk 6 sera, #211), a POI vaccinated calf [1 mg POI with complete Freund's adjuvant (CFA) primary+2 boosters (3 wk interval) and 1 booster with incomplete CFA (ICFA), wk 10 serum, #212], and a FI vaccinated calf (125 $\mu$g FI with CFA+1 booster at wk 3 with CFA, wk 6 serum, #274). Negative control serum was made as a pool of 50 sero-negative calves.

Molecular Sieve Chromatography

POI proteins were fractionated by molecular size using a SEPHACRYL S-300 (Pharmacia Biotech, Piscataway, N.J.) high resolution molecular sieve column. The column was calibrated using as molecular weight standards, ovalbumin (45 kDa), bovine serum albumin (68 kDa), bovine IgG (150 kDa), and blue dextran ($1.5\times10^6$ kDa). Ten ml fractions were collected and pooled for SDS-PAGE analysis.

Reversed-Phase High-Performance Liquid Chromatography (HPLC)

POI fractions were further fractionated using reverse-phase HPLC with a Waters $\mu$BONDAPAK C18 (3.9×300 mm) column (Waters, Milford, Mass.). Sample elution was monitored at 280 nm with a Waters Lambda-Max Model 481 LC spectrophotometer (Waters). Proteins were eluted at a flow rate of 1 ml/min over a 45 min linear gradient of 100% buffer A (0.1% trifluoroacetic acid in $H_2O$) to 100% buffer B (0.085% trifluoroacetic acid containing 70% acetonitrile in $H_2O$).

Continuous Elution SDS-PAGE Electrophoresis

The 16 kDa protein was purified from the molecular sieve fraction IV (FIV) utilizing continuous elution SDS-PAGE with the Bio-Rad 491 prep cell according to the manufacturers instructions. FIV proteins were lyophilized and reconstituted with SDS-PAGE sample buffer containing SDS and 5% 2-ME (Pruett & Thomas, 1986, ibid). A 37 mm diameter column was used for polypeptide separation with a 6 cm high 16% polyacrylamide gel (30.0:0.8, acrylamide:bis-acrylamide). The sample was loaded onto the stacking gel (10%) and the run conducted at 40 mAmps constant current. Continuous elution fractions (2.5 ml, 128 total) were collected and subjected to gradient SDS-PAGE analysis for purity.

Amino Terminal Sequencing

Purified 16 kDa protein was submitted to the Biotechnology Instrumentation Facility, Peptide and Protein Technologies, Department of Entomology, Texas A&M University, for amino terminal sequencing. The 16 kDa protein was subjected to Edman chemistry by the method indicated (Method 3.4) on the Sequence Sample Information Sheet for the Hewlett Packard G1005A Protein Sequencing System for 30 cycles. A 26 amino acid sequence segment of the 16 kDa protein (aa 2–27) was submitted to a computer assisted similarity search using BLASTP (Altschul, et al., 1990, J. Mol. Biol., 215:403–410) an algorithm that compares an amino acid query sequence against a protein database.

Cloning and Sequencing of *P. ovis* cDNA Gene Specifying the 16 kDa Protein.

Mites were collected from animals, rinsed with 10 mM Tris-HCl containing 25 mM EDTA, pH 7.5, and stored in liquid nitrogen until use. Total RNA was isolated from 1.6–8.0 g frozen mites by grinding in a Tenbroeck tissue grinder with RNA ISOLATOR purchased from Genosys Biotechnologies, Inc. (The Woodlands, Tex.) and precipitated with ethanol. Optimized yield of mite RNA was approximately 0.2% (w/w) with respect to mites. Messenger RNA was separated from total RNA using the POLYTRACT mRNA isolation kit (Promega Corp., Madison, Wis.). Messenger RNA integrity was tested by in vitro translation using a nuclease-treated rabbit reticulocyte system (Promega) with [S-35]-labeled methionine and polyacrylamide gel electrophoresis as previously described (Temeyer and Pruett, 1990, Annals of Entomol. Soc. Amer., 83:55–58). Canine pancreatic microsomes (Promega) were sometimes added to the in vitro translation reactions to assess signal peptide cleavage and glycosylation. Double stranded CDNA (ds-CDNA) was synthesized from messenger RNA template using the SUPERSCRIPT CHOICE kit (Life Technologies, Inc., Gaithersburg, Md.). Not I/EcoR I adapters were ligated onto the ends of the ds-cDNA and unincorporated adapters were removed by sephadex column chromatography. cDNA was then ligated to lambda-ZIPLOX EcoR I arms (Life Technologies, Inc.) and packaged into lambda phage using the PACKAGENE Lambda DNA Packaging System (Promega) or MAXPLAX packaging extract (Epicentre Technologies, Madison, Wis.). The resulting cDNA libraries were titered on LB-agar plates containing ampicillin at 100 micrograms per ml using *E. coli* Y1090(ZL) as the recipient host strain. The first 90 nucleotides of cloned cDNA specifying *P. ovis* 16 kDa protein was amplified by PCR using a series of degenerate oligonucleotide primers designed from the reverse translated amino sequence (FIG. 2) and sequenced using a SEQUENASE DNA sequencing kit (Amersham) by standard techniques. Oligonucleotide primers used for PCR and DNA sequencing were designed by selecting specific regions of the reverse translated sequence which exhibited no or low sequence homology to other regions of the reverse translated sequence or to known sequences of Drosophila DNA obtained from GenBank. Oligonucleotide primers were synthesized (see Tables 1 and 2) which exhibited melting temperatures (calculated by Oligo Primer Design Software (National BioSciences Inc., Plymouth, Minn.) in the range of 47–65° C., which contained at least two nondegenerate nucleotides at their 3'-ends, and which lacked homology at their 3'-ends to their own internal sequence, or that of other primers used together in PCR primer pairs. An additional primer (T15-15) was synthesized with incomplete homology to the known adapter sequence which had been ligated to the 3'-ends of the dscDNA during cDNA library construction and was used together in PCR primer pairs with selected 16kDa-specific primers to obtain overlapping PCR-amplified fragments of the 16kDa cDNA. These overlapping PCR products were electrophoretically used to determine consensus nucleotide distances to both ends of the cDNA genes represented in the cDNA library and to assess the specificity of the PCR primers for subcloning and sequencing. The 90 base pair cDNA nucleotide fragment corresponding to the reverse translion of the first 30 N-terminal amino acids of the *P. ovis* 16 kDa protein was cloned and sequenced to resolve ambiguities present in the reverse translation of the amino acid sequence. The unambiguous nucleotide sequence obtained was in perfect agreement with that predicted by reverse translation and was used to design nonredundant oligonucleotide primers for cloning and sequencing adjacent regions of the cDNA specifying the *P. ovis* 16kDa protein. The criteria used in oligonucleotide primer design were similar to that used previously with regard to Tm and the lack of homology of their 3'-ends with known sequences or other primers (Table 2). Sequencing primers were also synthesized specific for cloning vector sequences flanking the cloned cDNA inserts. As the known sequence was extended in both directions, new primers were synthesized based on newly revealed sequence data to continue extending the known sequence until both strands of the entire cDNA gene had been sequenced (FIG. 3).

As shown in FIG. 3, the underlined sequence corresponds to the reverse translation of the 30 N-terminal amino acids obtained by microsequencing the isolated 16 kDa protein of *P. ovis.* Sequence in bold type is translated to the predicted mature *P. ovis* 16 kDa protein with an additional 16–17 amino acid peptide leader sequence commencing with two tandem translational start codons specified by the italic type (beginning with ATGATG . . . ). The leader sequence is consistent with a signal sequence expected for a secreted protein.

Immunization of Cattle with the 16 kDa Protein

Hereford steers (12, at 150–200 kg) were used in the 16 kDa immunization experiment. These calves were purchased from a local auction barn (Gillespie Livestock, Fredericksburg, Tex). Upon arrival at the Knipling-Bushland U.S. Livestock Insect Research Laboratory the calves were inprocessed. Briefly, they were dewormed, vaccinated, and sprayed with 0.3% coumaphos to kill residual ectoparasites. The calves were randomly assigned to 4 experimental groups. Group 1 was vaccinated with a 25 μg/dose; Group 2, a 10 μg/dose; Group 3, a 5 μg/dose; and Group 4, the sham vaccinated controls, received adjuvant only. An animal use protocol was submitted and approved by the KBUSLIRL, Institutional Animal Care and Use Committee.

The 16 kDa protein, isolated with the Bio-Rad 491 prep cell, was stored in buffer containing 0.025 M Tris, 0.192 M glycine, pH 8.3, and 0.1% SDS. The protein concentration was determined using a BCA kit according to the manufacturers instructions (Pierce, Rockford, Ill.). The veterinary acceptable adjuvant used in this experiment was a mixture of alhydrogel and amphigen (A/A). The 16 kDa protein was adsorbed to alhydrogel (E. M. Sergeant Pulp and Chemical Co., Inc., Clifton, N.J., 12% by weight) as described previously (Pruett and Stromberg, 1995, Vet. Parasitol., 58:143–153). Briefly, the 16 kDa protein was adsorbed overnight at 4° C. in a 0.01 M sodium phosphate buffer, pH 6.5. The following morning amphigen (MRKS Marketing Services Ltd., Elkhorn, Nebr. 5% by volume) base (amphigen 1 volume: 3 volumes drakeol 5, Penreco, Dickenson, Tex.) was added to the adsorbed 16 kDa protein and emulsified. Injections were administered subcutaneously in a 2.0 ml volume. The primary injection was given on the first day of the experiment and a booster injection was given on day 21 of the experiment. The calves were skin tested on d 14 following the booster injection.

Intradermal Skin Testing

Calves vaccinated with the 16 kDa protein were skin tested by intradermal injection of the 16 kDa protein. Calves were injected intradermally with 0.1 ml containing 1 μg of 16 kDa protein in 0.010 M phosphate buffered saline (PBS, pH 7.2, 0.85% NaCl). Control injection sites included a PBS control and a separate PBS containing 0.1% SDS injection site. The diameter of the skin reaction was measured at 0.5, 1.0, 4, 24, and 48 h. The area of the skin reaction was determine by $A=\Pi(r^2)$ and reported in $mm^2$.

Results

Soluble protein extracts (n=22) of homogenized mites yielded 7.0±1.3% protein by weight. SDS-PAGE (3–22%) gradient resolution of the polypeptides of POI yielded numerous, poorly resolved, bands distributed from high to low molecular weights. These results suggested a low yield of any particular protein resulting from the homogenization of mites. Many of the polypeptides in POI were antigenic as demonstrated by immunoblotting using immune sera from infested calves. Polypeptide bands in the region of 30 kDa and 16 kDa were consistently recognized by antibodies in the serum of infested calves.

POI was fractionated on a DEAE anion-exchange column using a linear NaCl gradient from 0.0 M to 1.0 M. The fractionated proteins were divided into 6 fractions (FI-FVI). FI proteins were representative of the fall through fraction. Several FI antigens were identified by immunoblotting. Immunodominant antigens were noted at 43, 30, and<20 kDa. SDS-PAGE and GelScan XL analysis of the F1 fraction revealed that the fraction contained at least 18 polypeptide bands that ranged in molecular weight from 208 kDa to 14 kDa, and with pI values that ranged from 5.38 to 9.04. Seven of the polypeptides had pI values above 7.0 (data not shown).

FI proteins were separated into 7 principal peaks (PI-PVII) by analytical reverse-phase (C-18) chromatography. These HPLC peaks were further analyzed by SDS-PAGE. Peaks IV through VII contained 6 principal polypeptides of molecular weights below 20 kDa. Immunoblot analysis of these protein fractions with infested calf serum revealed 2 principal antigens, most prominent in peak VI at approximate molecular weights of 30 and 16 kDa.

Having determined that 2 principal antigens were<40 kDa, POI was fractionated by S-300 column chromatography for the purpose of concentrating and separating the proteins of interest from the many other *P. ovis* proteins in POI. POI was fractionated into 6 fractions (FI-FVI) using S-300 molecular sieve chromatography. These fractions were further analyzed by SDS-PAGE and immunoblotting. Fraction IV (FIV) was found to contain polypeptides of<40 kDa. Immunoblot results with immune serum from a calf vaccinated with POI demonstrated exceptionally intense antibody binding to a polypeptide band in the 16 kDa range.

GelScan XL analysis of SDS-PAGE separated FIV proteins revealed 9 principal peaks. These proteins ranged in molecular weight from 35 kDa to 15 kDa. The 16–17 kDa band represented 38% of the total protein. FIV proteins were further fractionated with analytical HPLC (C-18). FIV proteins were separated into 5 principal peaks (PI-PV) by HPLC. Immunoblot results suggested that the 16 kDa protein was predominantly in peak 4, but could not be obtained in pure form as a polypeptide of approximately 13 kDa co-eluted.

Purification of the 16 kDa protein was accomplished by preparative SDS-PAGE continuous elution gel electrophoresis of FIV (molecular sieve) proteins, with a Bio-Rad 491 Prep Cell apparatus. Tubes containing pure 16 kDa protein (determined by SDS-PAGE) were pooled and stored frozen for further analysis.

Immunoblot analysis demonstrated antibody binding (high titer) to the 16 kDa protein in the serum of a FI vaccinated calf, and in the serum (low titer) of a control infested calf.

Pure 16 kDa protein was sequenced for 30 cycles with the Hewlett Packard G1005A Protein Sequencing System using Edman chemistry. The amino acid sequence of the first 30 amino acids of the 16 kDa protein was reported as G>S>VKVKFQDCGKGEVESLEVEGCSGDYCVI?HK. Glycine was called as amino acid 1, with isoleucine as a questionable call at amino acid position 28. The last 5 cycles were accompanied by considerable lag and background, thus confidence in their call was reduced.

A 26 amino acid sequence segment of the 16 kDa protein (aa 2–27) was submitted to a similarity search using BLASTP. The 16 kDa amino acid sequence was compared to 260,575 different sequences deposited in GenBank, CDS translations, PDB, SwissProt, Spupdate, and PIR. Significant sequence homology ($P=2.2\times10^{-7}$) was observed with the principal allergen Lep d I of the storage mite *Lepidoglyphus destructor,* and the Der f II house-dust mite allergen from *Dermatophagoides farinae* (FIG. 5) Alignment with Lep d I [gi|999458 (X83875)] yielded 61% identities and 76% positives when considering conservative changes. Alignment with Der f II (pir|A61501) yielded 36% identities, and 63% positives when considering conservative changes (P=0.39).

The 143 amino acid sequence (FIG. 4) deduced from the cDNA sequence was submitted to a similarity search using BLASTP 2.0.4 (Altschul et al., 1997, Gapped BLAST and PSI-BLAST: A new generation of protein database search programs, Nucleic Acids Res., 25:3389–3402) and was compared to 306,190 different protein sequences compiled from GenBank, CDS translations, PDB, SwisProt, SPupdate and PIR. Significant amino acid sequence homology was found to the principal allergen Lep D I of *Lepidoglyphus destructor* ($P=3\times10^{-28}$), the group 2 allergen of *Tyrophagus putrescentiae* ($P=6\times10^{-26}$) and the Der f II major allergen of *Dermatophagoides farinae* ($P=6\times10^{-23}$). Alignment with Lep D I precursor [sp|P80384|LEP1 LEPDS] yielded 52/127=40% amino acid identities and 80/127=62% positive similarities (including conservative amino acid substitutions). Alignment with the Der f II major allergen of *D. farinae* [bbs|148475] yielded 43/100=43% amino acid identities and 70/100=70% positive similarities. Alignment with the group 2 allergen of *T. putrescentiae* [gnl|PID|e315131] yielded 44/127=34% amino acid identities and 78/127=60% positive similarities.

The complete cDNA sequence (FIG. 3) was also submitted to a similarity search using BLASTN 1.4.11 [Nov. 24, 1997}(Altschul et al., 1990. Basic local alignment search tool, J. Mol. Biol., 215:403–410) and was compared to 343,316 nucleotide sequences consisting of 706,578,648 total nucleotides. Significant homology was found to *L. destructor* mRNA for Lep D I allergen with 204/358=56% nucleotide identities ($P=8.4\times10^{-25}$), *D. farinae* mRNA for mite allergen Der f II with 133/227=58% nucleotide identities ($P=7.8\times10^{-14}$) and *T. putrescentiae* mRNA for group 2 allergen with 167/319=52% nucleotide identities ($P=2.6\times10^{-10}$).

Intradermal skin test results of calves vaccinated with different dosages of 16 kDa protein are presented in FIG. 6. Tissue fixed specific anti-16 kDa protein antibody was demonstrated by intradermal injection of purified 16 kDa protein. The 16 kDa protein formulated with A/A elicited immediate-type hypersensitivity responses in all vaccinated calves regardless of immunization dose. Skin swelling at the injection site declined rapidly after 1 hour.

Discussion

Knowledge of the immunogenicity/allergenicity of purified *P. ovis* proteins in cattle is limited. In an effort to qualitatively describe mite proteins to which cattle respond, Boyce and Brown (1991, ibid) electrophoretically resolved Psoroptes spp. crude soluble proteins from cattle collected mites. These separated proteins were immunoblotted with serum from a moderately P. spp. infested cow. They found that<20 antigens were recognized by antibodies in this serum, with bands at 10 and 116 kDa being most prominent. In the current study coomassie staining of SDS-PAGE resolved POI resulted in numerous poorly resolved polypeptide bands with several being antigenic as defined by immunoblotting with serum from an infested animal. Two immunodominant antigens were noted at molecular weights of <40 kDa, specifically, 30 and 16 kDa.

In a recent vaccine/challenge trial conducted at this laboratory naive calves vaccinated with a partially purified fraction of POI, designated as Fraction I (FI), were protected from infestation with *P. ovis.* A self-grooming behavioral response was believed to be the significant effector in protecting FI vaccinated calves. The grooming response among vaccinated calves was presumably heightened by a pruritic, immediate-type hypersensitivity response to FI allergens. Antigens of molecular weights (30 and 16 kDa) similar to those immunodominant proteins described in POI are found in FI.

Prior to infestation in the FI trial naïve calves vaccinated with a high dose (125μg+A/A) of FI were skin tested with FI antigens intradermally. These calves responded with an immediate hypersensitivity response (0.5–1.0hr). Their skin response, as a group, at 4–24 hr was heterogeneous. In contrast naïve calves vaccinated with a low dose (10μg+A/A) of FI expressed comparable 0.5–1.0 hr reaction, but had more intense and homogeneous 4–24 hr, late-phase responses. Although the low dose vaccinated calves had mite populations lower than control calves they experienced dermatitis comparable to the control group. It was speculated that a late-phase host response to *P. ovis* allergens may be responsible for host induced dermatitis. Eosinophil accumulation and degranulation in the local region of late-phase inflammation is a characteristic of the late-phase response (Solley et al., 1976, J. Clin. Invest., 58:408–420; Frew and Kay, 1988, J. Immunol., 141:4158–4164). Degranulation of eosinophils and the subsequent release of cationic granular proteins can account for tissue damage (Frigas and Gleich, 1986, J. Allergy Clin. Immunol., 77:527–537). Therefore, from these results it was reasoned that the best candidate vaccine antigen, one having the potential to reduce mite population and limit host dermatitis, should be an antigen that would elicit a local immediate-type hypersensitivity response, encouraging host grooming behavior, without eliciting the subsequent late-phase response.

Of the 2 immunodominant proteins observed in FI (30 and 16 kDa) the 16 kDa protein was chosen for initial purification and immunological analysis. Preliminary serological and immunoblot results suggest that the 30 kDa protein may be involved in cross reactions with antibodies elicited by host exposure to other ectoparasite species. Tropomyocin is a 36 kDa invertebrate muscle protein that is a known major shrimp allergen (Shanti et al., 1993, J. Immunol., 151:5354–5363) and elicits antibodies that cross react with other invertebrate allergens (Witteman, et al., 1994, Arch. Allergy Immunol., 105:56–61).

The 16 kDa protein is of relatively low concentration in FI. However, molecular sieve chromatography of the crude *P. ovis* proteins and pooling of proteins of<40 kDa resulted in a fraction (FIV) that was ~38% of total protein as 16 kDa. Purification of the 16 kDa protein from FIV was attempted using reverse-phase HPLC (C18) chromatography. However, the 16 kDa protein could not be purified to single band purity with HPLC. A 13 kDa band consistently coeluted with the 16 kDa protein. Purification of the 16 kDa protein to single band purity was eventually accomplished with continuous elution SDS-PAGE using the Bio-Rad 491 prep cell apparatus.

The purified 16 kDa protein was found to be immunogenic in cattle when administered with A/A as adjuvant even at the low dose of 5 μg. The results of intradermal skin testing with the 16 kDa protein elicited intense antibody-mediated immediate hypersensitivity reactions that subsided after 1 hr. No measurable late-phase activity was observed. The allergenic nature of the 16 kDa protein was further supported by sequence homology with known mite allergens Lep dI from the storage grain mite *L. destructor* and Der f II from the dust mite *D. farinae* (Varela, et al., 1994, Eur. J. Biochem., 225:93–98). The function of the group II (Der f II) house dust mite allergens is unknown, however, a lysozyme-like activity has been proposed for Der f II based upon chemico-physical property homologies, but has not been proven (Stewart, et al., 1992, J. Allergy Clin. Immunol. 90:141–142). There is ~80% conservation of identity of the amino acid sequence among the 25 kDa acidic-neutral proteins of the Group I house dust mite allergens and 4 of the major group I house dust mite allergens are enzymes (Robinson et al., 1997, Clin. Exp. Allergy, 27:10–21). Considering the homology between the 16 kDa *P. ovis* protein and the group 2 allergens Der f II and Lep d I, it may be that these proteins represent similar and conserved function.

These data suggest that the 16 kDa *P. ovis* protein is allergenic in cattle in that when formulated with A/A as adjuvant it elicits an immediate hypersensitivity response. In addition, it does not appear, in this formulation, to elicit the potential tissue destructive late-phase response.

It is understood that the foregoing detailed description is given merely by way of illustration and that modifications and deviations may be made therein without departing from the spirit and scope of the invention.

TABLE 1

Synthesis of Initial Oligonucleotide Primers for PCR and Sequencing

| Name | Sequence (5'-->3') | Position[a] | Length | Tm |
|---|---|---|---|---|
| R16K19-23 | TCNACYTCNCCYTTNCCRCARTC | 41-->19 | 23 | 59.4 |
| R16K52-23 | TARTCNCCNSWRCANCCYTCNAC | 74-->52 | 23 | 57.1 |
| R16K71-21 | YTTRTGDATNACRCARTARTC | 99-->70 | 21 | 47.9 |

TABLE 1-continued

Synthesis of Initial Oligonucleotide Primers for PCR and Sequencing

| Name | Sequence (5'-->3') | Position[a] | Length | Tm |
|---|---|---|---|---|
| F16K20-20 | GGNAARGTNAARTTYCARGA | 1-->20 | 20 | 51.5 |
| F16K38-23 | CARGAYTGYGGNAARGGNGARGT | 16-->38 | 23 | 63.2 |
| F16K80-26 | GARGGNTGYWSNGGNGAYTAYTGYGT | 55-->80 | 26 | 65.3 |
| F16K89-23 | GGNGAYTAYTGYGTNATHCAYAA | 67-->89 | 23 | 54.8 |
| T16K15-15 | CCTCGCGGCCTCGTC | adapter | 15 | 67.4 |

[a]Relative to Position 1 of the + strand specifying N-terminal amino acids 1–30

TABLE 2

Synthesis of Oligonucleotide Primers for PCR and Sequencing

| Name | Sequence | Position[a] | Length | Tm |
|---|---|---|---|---|
| F16K1-24 | GGGAAGGTCAAGTTTCAAGACTGT | 1-->24 | 24 | 65.4• |
| F16K21-30 | CTGTGGAAAAGGGGAAGTTGAATCTCTTGA | 21-->50 | 30 | 73.1• |
| 157U23 | ATTGTTGCCGATATCAACGGTGT | 157-->179 | 23 | 68• |
| 177U27 | TGTACAAATTGAAGTTCCTGGCGTTGA | 177-->203 | 27 | 71.3• |
| 284U22 | CAATCTTGCCAACTACCAAAGC | 284-->305 | 22 | 64.5• |
| R16K34-30 | ACAGCCTTCGACTTCAAGAGATTCAACTTC | 63-->34 | 30 | 71.3• |
| R16K60-22 | GACGCAGTAGTCACCTGAACAG | 81-->60 | 22 | 63.8• |
| 127L28 | CGAGTTTCAAATTGGCTGAATCTTGGTT | 154-->127 | 28 | 71.5• |
| 184L27 | ATCATGATCAACGCCAGGAACTTCAAT | 206-->184 | 27 | 71.5• |
| 286L24 | TTTAGCTTTGGTAGTTGGCAAGAT | 309-->286 | 24 | 63.6• |

[a]Relative to Position 1 of the + strand specifying N-terminal amino acids 1–30

We claim:

1. A method for protecting bovine against *Psoroptes ovis* comprising administering an isolated protein to said bovine in an amount effective to elicit a local immediate-type hypersensitivity response against *Psoroptes ovis* therein, wherein said protein comprises the amino acid sequence:

$X_1$KVKFQDCGKGEVESLEVEGCSGDYCVIHKGKK-LDLAI SVTSNQDSANLKLDIVADING VQIEVPGVDHDGCHYVKCPIKKGQHFD-VKYTYSIPAILPTTKAKIIAKIIGDKGLGGCIV INGEIQD (SEQ ID No. 1)

wherein said $X_1$ is selected from the group consisting of G, S, and V.

2. The method of claim 1 wherein said bovine comprises cattle.

3. The method of claim 1 wherein said administering of said protein does not elicit a late phase immune response in said bovine.

* * * * *

SEQUENCE LISTING

```
<160> NUMBER OF SEQ ID NOS: 25

<210> SEQ ID NO 1
<211> LENGTH: 126
<212> TYPE: PRT
<213> ORGANISM: Psoroptes ovis
<220> FEATURE:
<221> NAME/KEY: VARIANT
<222> LOCATION: (1)
<223> OTHER INFORMATION: X at position 1 may also be G or S or V

<400> SEQUENCE: 1

Xaa Lys Val Lys Phe Gln Asp Cys Gly Lys Gly Glu Val Glu Ser Leu
  1               5                  10                  15

Glu Val Glu Gly Cys Ser Gly Asp Tyr Cys Val Ile His Lys Gly Lys
             20                  25                  30

Lys Leu Asp Leu Ala Ile Ser Val Thr Ser Asn Gln Asp Ser Ala Asn
         35                  40                  45

Leu Lys Leu Asp Ile Val Ala Asp Ile Asn Gly Val Gln Ile Glu Val
```

-continued

```
     50                  55                  60

Pro Gly Val Asp His Asp Gly Cys His Tyr Val Lys Cys Pro Ile Lys
 65                  70                  75                  80

Lys Gly Gln His Phe Asp Val Lys Tyr Thr Tyr Ser Ile Pro Ala Ile
                 85                  90                  95

Leu Pro Thr Thr Lys Ala Lys Ile Ile Ala Lys Ile Ile Gly Asp Lys
            100                 105                 110

Gly Leu Gly Gly Cys Ile Val Ile Asn Gly Glu Ile Gln Asp
        115                 120                 125


<210> SEQ ID NO 2
<211> LENGTH: 588
<212> TYPE: DNA
<213> ORGANISM: Psoroptes ovis

<400> SEQUENCE: 2

cctcgcggcc tcgtcgaccc caattaaaac taaaaaataa ttttaaaaaa atcaaaatga     60

tgaaaacttt ggtagttctc gccatcactt tggctgttgt atcagctggs aargtcaart    120

tycaagactg tggaaaaggr gaagttgaat ctcttgaagt tgaaggctgt tcaggtgatt    180

actgcgtcat tcacaaaggt aaaaaacttg atttagccat cagtgtaaca tcgaaccaag    240

attcagccaa tttgaaactc gatattgttg ccgatatcaa cggtgtacaa attgaagttc    300

ctggcgttga tcatgatggt tgccattacg tcaaatgtcc aatcaagaaa ggccaacact    360

ttgacgtcaa atacacatac agcattccag caatcttgcc aactaccaaa gctaaaatca    420

ttgctaaaat tattggtgat aaaggtcttg gtggttgtat cgtaatcaat ggtgaaattc    480

aagactaaat caataaaaac ctaaaaatat tttgatgaaa ttagatttgt tatttttatt    540

tctcatttta ttcaaaatta aaaagtattc agtcgacgag gccgcgag                 588


<210> SEQ ID NO 3
<211> LENGTH: 143
<212> TYPE: PRT
<213> ORGANISM: Psoroptes ovis

<400> SEQUENCE: 3

Met Met Lys Thr Leu Val Val Leu Ala Ile Thr Leu Ala Val Val Ser
  1               5                  10                  15

Ala Gly Lys Val Lys Phe Gln Asp Cys Gly Lys Gly Glu Val Glu Ser
            20                  25                  30

Leu Glu Val Glu Gly Cys Ser Gly Asp Tyr Cys Val Ile His Lys Gly
        35                  40                  45

Lys Lys Leu Asp Leu Ala Ile Ser Val Thr Ser Asn Gln Asp Ser Ala
     50                  55                  60

Asn Leu Lys Leu Asp Ile Val Ala Asp Ile Asn Gly Val Gln Ile Glu
 65                  70                  75                  80

Val Pro Gly Val Asp His Asp Gly Cys His Tyr Val Lys Cys Pro Ile
                 85                  90                  95

Lys Lys Gly Gln His Phe Asp Val Lys Tyr Thr Tyr Ser Ile Pro Ala
            100                 105                 110

Ile Leu Pro Thr Thr Lys Ala Lys Ile Ile Ala Lys Ile Ile Gly Asp
        115                 120                 125

Lys Gly Leu Gly Gly Cys Ile Val Ile Asn Gly Glu Ile Gln Asp
    130                 135                 140


<210> SEQ ID NO 4
```

-continued

<211> LENGTH: 90
<212> TYPE: PRT
<213> ORGANISM: Psoroptes ovis

<400> SEQUENCE: 4

```
Gly Gly Asn Ala Ala Arg Gly Thr Asn Ala Ala Arg Thr Thr Tyr Cys
  1               5                  10                  15

Ala Arg Gly Ala Tyr Thr Gly Tyr Gly Gly Asn Ala Ala Arg Gly Gly
             20                  25                  30

Asn Gly Ala Arg Gly Thr Asn Gly Ala Arg Trp Ser Asn Tyr Thr Asn
         35                  40                  45

Gly Ala Arg Gly Thr Asn Gly Ala Arg Gly Gly Asn Thr Gly Tyr Trp
     50                  55                  60

Ser Asn Gly Gly Asn Gly Ala Tyr Thr Ala Tyr Thr Gly Tyr Gly Thr
 65                  70                  75                  80

Asn Ala Thr His Cys Ala Tyr Ala Ala Arg
                 85                  90
```

<210> SEQ ID NO 5
<211> LENGTH: 90
<212> TYPE: PRT
<213> ORGANISM: Psoroptes ovis

<400> SEQUENCE: 5

```
Cys Cys Asn Thr Thr Tyr Cys Ala Asn Thr Thr Tyr Ala Ala Arg Gly
  1               5                  10                  15

Thr Tyr Cys Thr Arg Ala Cys Arg Cys Cys Asn Thr Thr Tyr Cys Cys
             20                  25                  30

Asn Cys Thr Tyr Cys Ala Asn Cys Thr Tyr Trp Ser Asn Arg Ala Asn
         35                  40                  45

Cys Thr Tyr Cys Ala Asn Cys Thr Tyr Cys Cys Asn Ala Cys Arg Trp
     50                  55                  60

Ser Asn Cys Cys Asn Cys Thr Arg Ala Thr Arg Ala Cys Arg Cys Ala
 65                  70                  75                  80

Asn Thr Ala Asp Gly Thr Arg Thr Thr Tyr
                 85                  90
```

<210> SEQ ID NO 6
<211> LENGTH: 26
<212> TYPE: PRT
<213> ORGANISM: Lepidoglyphus destructor

<400> SEQUENCE: 6

```
Lys Met Thr Phe Lys Asp Cys Gly His Gly Glu Val Thr Glu Leu Asp
  1               5                  10                  15

Ile Ser Gly Cys Ser Gly Asp Thr Cys Val
             20                  25
```

<210> SEQ ID NO 7
<211> LENGTH: 22
<212> TYPE: PRT
<213> ORGANISM: Dermatophagoides farinae

<400> SEQUENCE: 7

```
Gln Val Asp Val Lys Asp Cys Ala Asn Asn Glu Ile Lys Lys Val Met
  1               5                  10                  15

Val Asp Gly Cys His Gly
             20
```

-continued

```
<210> SEQ ID NO 8
<211> LENGTH: 23
<212> TYPE: PRT
<213> ORGANISM: Psoroptes ovis

<400> SEQUENCE: 8

Thr Cys Asn Ala Cys Tyr Thr Cys Asn Cys Cys Tyr Thr Thr Asn Cys
  1               5                  10                  15

Cys Arg Cys Ala Arg Thr Cys
             20


<210> SEQ ID NO 9
<211> LENGTH: 23
<212> TYPE: PRT
<213> ORGANISM: Psoroptes ovis

<400> SEQUENCE: 9

Thr Ala Arg Thr Cys Asn Cys Cys Asn Ser Trp Arg Cys Ala Asn Cys
  1               5                  10                  15

Cys Tyr Thr Cys Asn Ala Cys
             20


<210> SEQ ID NO 10
<211> LENGTH: 21
<212> TYPE: PRT
<213> ORGANISM: Psoroptes ovis

<400> SEQUENCE: 10

Tyr Thr Thr Arg Thr Gly Asp Ala Thr Asn Ala Cys Arg Cys Ala Arg
  1               5                  10                  15

Thr Ala Arg Thr Cys
             20


<210> SEQ ID NO 11
<211> LENGTH: 20
<212> TYPE: PRT
<213> ORGANISM: Psoroptes ovis

<400> SEQUENCE: 11

Gly Gly Asn Ala Ala Arg Gly Thr Asn Ala Ala Arg Thr Thr Tyr Cys
  1               5                  10                  15

Ala Arg Gly Ala
             20


<210> SEQ ID NO 12
<211> LENGTH: 23
<212> TYPE: PRT
<213> ORGANISM: Psoroptes ovis

<400> SEQUENCE: 12

Cys Ala Arg Gly Ala Tyr Thr Gly Tyr Gly Gly Asn Ala Ala Arg Gly
  1               5                  10                  15

Gly Asn Gly Ala Arg Gly Thr
             20


<210> SEQ ID NO 13
<211> LENGTH: 26
<212> TYPE: PRT
<213> ORGANISM: Psoroptes ovis

<400> SEQUENCE: 13

Gly Ala Arg Gly Gly Asn Thr Gly Tyr Trp Ser Asn Gly Gly Asn Gly
  1               5                  10                  15
```

-continued

```
Ala Tyr Thr Ala Tyr Thr Gly Tyr Gly Thr
             20                  25


<210> SEQ ID NO 14
<211> LENGTH: 23
<212> TYPE: PRT
<213> ORGANISM: Psoroptes ovis

<400> SEQUENCE: 14

Gly Gly Asn Gly Ala Tyr Thr Ala Tyr Thr Gly Tyr Gly Thr Asn Ala
  1               5                  10                  15

Thr His Cys Ala Tyr Ala Ala
             20


<210> SEQ ID NO 15
<211> LENGTH: 15
<212> TYPE: DNA
<213> ORGANISM: Psoroptes ovis

<400> SEQUENCE: 15

cctcgcggcc tcgtc                                                    15


<210> SEQ ID NO 16
<211> LENGTH: 24
<212> TYPE: DNA
<213> ORGANISM: Psoroptes ovis

<400> SEQUENCE: 16

gggaaggtca agtttcaaga ctgt                                          24


<210> SEQ ID NO 17
<211> LENGTH: 30
<212> TYPE: DNA
<213> ORGANISM: Psoroptes ovis

<400> SEQUENCE: 17

ctgtggaaaa ggggaagttg aatctcttga                                    30


<210> SEQ ID NO 18
<211> LENGTH: 23
<212> TYPE: DNA
<213> ORGANISM: Psoroptes ovis

<400> SEQUENCE: 18

attgttgccg atatcaacgg tgt                                           23


<210> SEQ ID NO 19
<211> LENGTH: 27
<212> TYPE: DNA
<213> ORGANISM: Psoroptes ovis

<400> SEQUENCE: 19

tgtacaaatt gaagttcctg gcgttga                                       27


<210> SEQ ID NO 20
<211> LENGTH: 22
<212> TYPE: DNA
<213> ORGANISM: Psoroptes ovis

<400> SEQUENCE: 20

caatcttgcc aactaccaaa gc                                            22
```

-continued

```
<210> SEQ ID NO 21
<211> LENGTH: 30
<212> TYPE: DNA
<213> ORGANISM: Psoroptes ovis

<400> SEQUENCE: 21

acagccttcg acttcaagag attcaacttc                                    30


<210> SEQ ID NO 22
<211> LENGTH: 22
<212> TYPE: DNA
<213> ORGANISM: Psoroptes ovis

<400> SEQUENCE: 22

gacgcagtag tcacctgaac ag                                            22


<210> SEQ ID NO 23
<211> LENGTH: 28
<212> TYPE: DNA
<213> ORGANISM: Psoroptes ovis

<400> SEQUENCE: 23

cgagtttcaa attggctgaa tcttggtt                                      28


<210> SEQ ID NO 24
<211> LENGTH: 27
<212> TYPE: DNA
<213> ORGANISM: Psoroptes ovis

<400> SEQUENCE: 24

atcatgatca acgccaggaa cttcaat                                       27


<210> SEQ ID NO 25
<211> LENGTH: 24
<212> TYPE: DNA
<213> ORGANISM: Psoroptes ovis

<400> SEQUENCE: 25

tttagctttg gtagttggca agat                                          24
```